United States Patent [19]

Akada et al.

[11] Patent Number: 4,475,992

[45] Date of Patent: Oct. 9, 1984

[54] CYCLOHEXADIENE DERIVATIVES AND PROCESS FOR PREPARING THE SAME

[75] Inventors: Mitsuo Akada; Tsunehiko Masatomi, both of Itano; Yasuo Shimizu, Tokushima; Shigeru Torii, Akaiwa; Hideo Tanaka, Okayama, all of Japan

[73] Assignee: Otsuka Kagaku Yakuhin Kabushiki Kaisha, Japan

[21] Appl. No.: 500,949

[22] Filed: Jun. 3, 1983

Related U.S. Application Data

[62] Division of Ser. No. 394,912, Jun. 22, 1982, Pat. No. 4,429,164.

[30] Foreign Application Priority Data

Oct. 29, 1980 [JP] Japan ................................. 55-152632
Feb. 25, 1981 [JP] Japan ................................. 56-27474
Feb. 25, 1981 [JP] Japan ................................. 56-27475

[51] Int. Cl.$^3$ .............................................. C25B 1/00
[52] U.S. Cl. ................................................. 204/59 R
[58] Field of Search ..................................... 204/59 R

[56] References Cited

U.S. PATENT DOCUMENTS 4,203,811 5/1980 Cramer .................................. 204/78

FOREIGN PATENT DOCUMENTS 2547383 4/1977 Fed. Rep. of Germany .... 204/59 R

*Primary Examiner*—John F. Niebling
*Attorney, Agent, or Firm*—Larson and Taylor

[57] ABSTRACT

Cyclohexadiene derivatives represented by the formula (I)

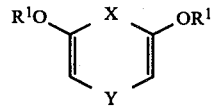

(wherein —X— represents

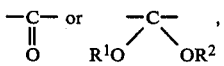

—Y— represents

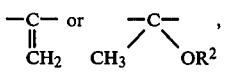

and $R^1$ and $R^2$ represent a lower alkyl group) and a process for preparing the same.

9 Claims, No Drawings

CYCLOHEXADIENE DERIVATIVES AND PROCESS FOR PREPARING THE SAME

This is a division of application Ser. No. 394,912 filed June 22, 1982, now U.S. Pat. No. 4,429,164.

TECHNICAL FIELD

This invention relates to novel cyclohexadiene derivatives and to a process for preparing the derivatives.

DISCLOSURE OF INVENTION

The cyclohexadiene derivatives of this invention are novel compounds which have not been disclosed heretofore in literature and which are represented by the formula (I)

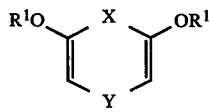

(I)

(wherein —X— represents

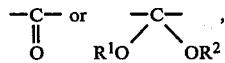

—Y— represents

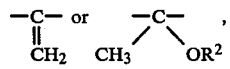

and $R^1$ and $R^2$ represent a lower alkyl group.)

Examples of the lower alkyl groups represented by $R^1$ and $R^2$ in the formula (I) are methyl, ethyl, n-propyl, isopropyl, n-butyl, sec-butyl, tert-butyl, etc.

The cyclohexadiene derivatives of the formula (I) are preapred for example by processes described below.

Among the derivatives of the formula (I), those in which —X— represents

and —Y— represents

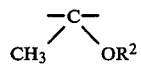

[namely those of the formula (Ia)] are prepared by electrolyzing a compound of the formula (II) given below (wherein $R^1$ and $R^2$ are as defined above) in the presence of a lower aliphatic alcohol and a neutral supporting electrolyte.

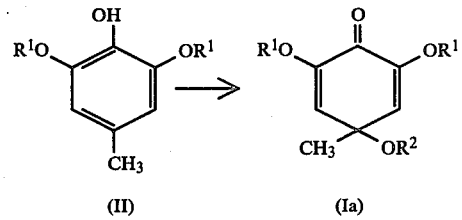

($R^1$ and $R^2$ in the above formulae are as defined above.)

The compounds of the formula (II) to be used as the starting material are known and relatively easily available. Useful compounds of the formula (II) include 2,6-dimethoxy-4-methylphenol, 2,6-diethoxy-4-methylphenol, 2,6-diisopropoxy-4-methylphenol, 2,6-dibutoxy-4-methylphenol, etc.

Examples of lower aliphatic alcohols useful in the foregoing electrolytic reaction are methanol, ethanol, isopropyl alcohol, n-butyl alcohol, etc. The amount of the lower aliphatic alcohol is not particularly limited but is suitably variable over a wide range. It is used in an amount of preferably 500 ml to 15 l, and especially preferably about 5 to about 10 l, per mole of the compound of the formula (II). The extra alcohol acts as the solvent.

Examples of useful neutral supporting electrolytes are quarternary ammonium salts such as p-toluenesulfonic acid tetramethylammonium salt, p-toluenesulfonic and tetraethylammonium salt, p-toluenesulfonic acid tetrabutylammonium salt and like p-toluenesulfonic acid tetraalkylammonium salts, and perchloric acid tetramethylammonium salt, perchloric acid tetrabutylammonium salt and like perchloric acid tetraalkylammonium salts, sodium formate, sodium acetate and like alkali metal salts of aliphatic carboxylic acid, sodium fluoride, potassium fluoride and like alkali metal fluorides, etc. The amount of the neutral supporting electrolyte to be used, although nonlimitative and suitably determinable over a wide range, is preferably about 0.01 to about 1 mole, and especially preferably about 0.1 to 0.5 mole, per mole of the compound of the formula (II). However, it is more preferred to determine the amount of the supporting electrolyte considering the reaction conditions and economy in view of the amount thereof affecting the voltage.

Preferred electrodes useful in the foregoing reaction are those made of titanium, platinum, carbon, lead dioxide, nickel or the like as the anode, and those made of platinum, carbon, titanium, nickel, stainless steel or the like as the cathode.

The required current density which is among the most important conditions is in the range of 1 to 200 mA/cm², preferably 5 to 100 mA/cm². A higher current density involved results in reduced current efficiency and in an increased amount of by-products. With a lower current density, a lower productivity results. Therefore, it is of greatest importance in electrolysis to determine optimum reaction conditions. The voltage to be applied in the foregoing electrolytic reaction ranges preferably from about 1.5 to about 15 V, more preferably from about 2 to about 5 V, although widely variable depending on the amount of the supporting electrolyte used.

The electrolytic temperature is in the range of preferably −10° to 50° C., more preferably 10° to 30° C.

With this invention, while the electrolytic reaction can be performed by using a diaphragm, electrolysis involving no diaphragm, which electrolysis is less costly, is also feasible, making it possible to manufacture compounds of the formula (Ia) on an industrial scale.

Among the cyclohexadiene derivatives of the formula (I), those in which —X— represents

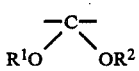

and —Y— represents

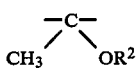

[namely those of the formula (Ib)] are prepared by electrolyzing a compound of the formula (III) given below in the presence of a lower aliphatic alcohol and a neutral or alkaline supporting electrolyte,

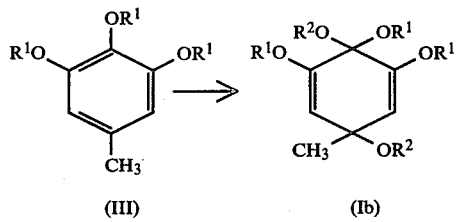

($R^1$ and $R^2$ in the above formulae are as defined above.)

The compounds of the formula (III) to be used as the starting material are known and relatively readily available. Specific examples of useful compounds of the formula (III) are 3,4,5,-trimethoxytoluene, 3,4,5-triethoxytoluene, etc.

Examples of lower aliphatic alcohols useful in the foregoing electrolytic reaction are methanol, ethanol, isopropyl, alcohol, n-butyl alcohol, etc. The amount of the lower aliphatic alcohol to be used is not particularly limited but can be appropriately selected within a wide range. It is used in an amount of preferably 500 ml to 15 l, especially preferably about 5 to 10 l, per mole of the compound of the formula (III).

Neutral or alkaline supporting electrolytes useful in the foregoing reaction include sodium hydroxide, potassium hydroxide, lithium hydroxide and like hydroxides of alkali metals, sodium, potassium and like alkali metals, tetramethylammonium hydroxide, tetraethylammonium hydroxide, tetrapropylammonium hydroxide, tetrabutylammonium hydroxide and like tetraalkylammonium hydroxides, etc. in addition to alkali metal salts of aliphatic carboxylic acid and alkali metal fluorides which are usable in the reaction for preparing the compound of the formula (Ia) by electrolyzing the compound of the formula (II). The amount of the supporting electrolyte to be used, although particularly nonlimitative and widely suitably variable over a wide range, is preferably about 0.01 to about 1 mole, especially preferably 0.1 to 0.5 mole, per mole of the compound of the formula (III). However, it is more preferred to determine the amount of the supporting electrolyte considering the reaction conditions and economy in view of the amount thereof affecting the voltage.

This electrolytic reaction can be performed at the same levels of the current density, applied voltage and electrolytic temperature as those employed in the reaction for preparing the compound of the formula (Ia) by electrolysis of the compound of the formula (II). The electrolytic reaction can be performed with use of the same electrode materials as those employed in the reaction for preparing the compound (Ia) as above mentioned.

Among the cyclohexadiene derivatives of the formula (I), those wherein —X— represents

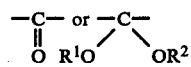

and —Y— represents

[namely those of the formula (Ic)] are prepared by treating a compound of the formula (IV) given below in the presence of an acid catalyst.

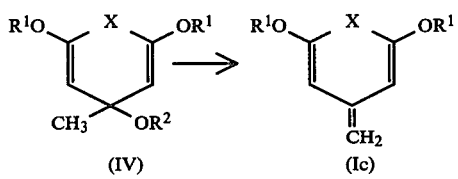

($R^1$ and $R^2$ in the above formulae are as defined above.)

Among the compounds of the formula (IV) serving as the starting material, those wherein —X— represents

correspond to those of the formula (Ia), while those wherein —X— represents

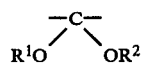

agree to those of the formula (Ib). Exemplary of the compounds of the formula (IV) are 2,4,6-trimethoxy-4-methyl-2,5-cyclohexadienone, 2,4,6-triethoxy-4-methyl-2,5-cyclohexadienone, 2,4,6-tripropoxy-4-methyl-2,5-cyclohexadienone, 2,4,6-tributoxy-4-methyl-2,5-cyclohexadienone,2,6-dimethoxy-4-ethoxy-4-methyl-2,5-cyclohexadienone, 2,6-dimethoxy-4-butoxy-4-methyl-2,5-cyclohexadienone, 2,6-diethoxy-4-propoxy-4-methyl-2,5-cyclohexadienone, 2,6-diethoxy-4-butoxy-4-methyl-2,5-cyclohexadienone, 2,6-dipropoxy-4-methoxy-4-methyl-2,5-cyclohexadienone, 2,6-dipropoxy-4-ethoxy-4,methyl-2,5-cyclohexadienone, 2,6-dibutoxy-4-methoxy-4-methyl-2,5-cyclohexadienone, 2,6dibutoxy-4-ethoxy-4-methyl-2,5-cyclohexadienone, 1,3,5,6,6-pentamethoxy-3-methyl-1,4-cyclohexadiene, 1,3,5,6,6-pentaethoxy-3-methyl-1,4-cyclohexadiene, 1,5,6-tributoxy-3,6-diethoxy-3-methyl-1,4-cyclohexadiene, etc.

Useful acid catalysts include compounds such as sulfuric acid, hydrochloric acid, hydrobromic acid, perhalogenic acid and like protonic acids, and aluminum chloride, zinc chloride, ferric chloride and like Lewis acids, etc. The amount of the catalyst to be used, although particularly nonlimitative and suitably determinable over a wide range, is usually about 0.5 to about 10% by weight, or about 1 to about 3% by weight which suffices from economical points of view, based on the weight of the compound of the formula (IV). In this reaction, a solvent is usable. Useful solvents include methylene chloride, chloroform, carbon tetrachloride and like hydrocarbon halides, benzene, toluene, xylene and like aromatic hydrocarbons, ethyl ether, isopropyl ether, butyl ether and like aliphatic ethers, n-hexane, n-pentane and like aliphatic hydrocarbons, etc. The amount of the solvent to be employed is not particularly limitative but can be suitably determined over a wide range. It is usually used in an amount of about 100 to about 3000 ml, and preferably about 1000 to about 2000 ml, per mole of the compound of the formula (IV). The reaction temperature allows a wide range of choice; for example about 0° to about 100° C. and particularly about 20° to about 50° C. are preferred. The reaction time is usually about 1 to about 12 hours, while about 3 to about 5 hours suffices.

Typical examples of the compounds of the formula (Ic) thus prepared are 2,6-dimethoxy-4-methylidene-2,5-cyclohexadienone, 2,6-diethoxy-4-methylidene-2,5-cyclohexadienone, 2,6-dipropoxy-4-methylidene-2,5-cyclohexadienone, 2,6-dibutoxy-4-methylidene-2,5-cyclohexadienone, 1,5,6,6-tetramethoxyl-3-methylidene-1,4-cyclohexadiene, 1,5,6,6-tetraethoxy-3-methylidene-1,4-cyclohexadiene, 1,5,6-trimethoxy-6-ethoxy-3-methylidene-1,4-cyclohexadiene, 1,5,6-triethoxy-6-methoxy-3-methylidene-1,4-cyclohexadiene, 1,5,6-tripropoxy-6-methoxy-3-methylidene-1,4-cyclohexadiene, etc.

The compounds of this invention can be purified by known means conventionally employed such as concentration, extraction, distillation, column chromatography, etc.

The present invention will be described below in detail with reference to examples given below.

EXAMPLE 1

A 182 mg quantity of 3,4,5-trimethoxytoluene and 20 mg of sodium hydroxide were dissolved in 10 ml of methanol. Electrolysis was carried out by immersing in the solution platinum electrodes as the anode and cathode each having an electrolytic area of 3 cm$^2$, stirring the solution at room temperature, and passing through the solution constant current of 30 mA at an electric charge of 3 F/mol and a terminal voltage of 3.5 to 3.7 V. After passing the current, the reaction liquid was concentrated at reduced temperature. The residue was extracted with dichloromethane and the extract was concentrated at reduced pressure, thereby recovering 255 mg of a crude product. The crude product was purified by alumina column chromatography using a 10:1 benzene-ethyl acetate mixture, giving 224 mg of 1,3,5,6,6-pentamethoxy-3-methyl-1,4-cyclohexadiene as white crystals in 92% of theoretical yield. The compound thus obtained was identified by NMR.

NMR (CDCl$_3$): δ1.44 (s, 3H, CH$_3$C), 3.13 (s, 3H, CH$_3$O), 3.18 (s, 3H, CH$_3$O), 3.30 (s, 3H, CH$_3$O), 3.68 (s, 6H, CH$_3$O—C=), 4.98 (s, 2H, HC=).

EXAMPLE 2

A 224 mg quantity of 3,4,5-triethoxytoluene and 20 mg of sodium fluoride were dissolved in 10 ml of ethanol. Electrolysis was conducted by immersing a carbon electrode as the anode and a stainless steel electrode as the cathode each having an electrolytic area of 3 cm$^2$, stirring the solution at room temperature and passing through the solution constant current of 30 mA at an electric charge of 3 F/mol. Subsequently the same procedure as in Example 1 was repeated producing 287 mg of 1,3,5,6,6-pentaethoxy-3-methyl-1,4-cyclohexadiene in 91.5% of theoretical yield. The compound thus obtained was identified by MNR.

NMR (CDCl$_3$): δ1.20 (m, 9H, CH$_3$), 1.35 (t, 6H, CH$_3$), 1.45 (s, 3H, CH$_3$C—), 3.40 (m, 6H, —CH$_2$—), 3.85 (q, 4H, CH$_3$OC=), 5.00 (s, 2H, HC=).

EXAMPLE 3

A 168 mg quantity of 2,6-dimethoxy-4-methylphenol and 30 mg of toluenesulfonic acid tetraethylammonium salt were dissolved in 10 ml of methanol. Electrolysis was effected by immersing platinum electrodes as the anode and cathode each having an electrolytic area of 3 cm$^2$, stirring the solution at room temperature and passing through the solution constant current of 30 mA at an electric charge of 3 F/mol and a terminal voltage of 3.5 to 3.7 V. After passing the current, the reaction liquid was concentrated at reduced pressure. The residue was extracted with dichloromethane and the extract was concentrated at reduced pressure, thereby recovering 190 mg of a crude product.

The crude product was purified by alumina column chromatography using a 10:1 benzene-ethyl acetate mixture, giving 188 mg of 2,4,6-trimethoxy-4-methyl-2,5-cyclohexadienone as white crystals in 95% of theoretical yield. The compound thus obtained was identified by MNR.

NMR (CDCl$_3$): δ1.53 (s, 3H, CH$_3$), 3.19 (s, 3H, CH$_3$O), 3.74 (s, 6H, CH$_3$OC=), 5.68 (s, 2H, HC=).

EXAMPLE 4

A 216 mg quantity of 2,6-diisopropoxy-4-methylphenol and 20 mg of sodium acetate were dissolved in 10 ml of ethanol. Electrolysis was performed by immersing a carbon electrode as the anode and a platinum electrode as the cathode each having an electrolytic area of 3 cm$^2$, stirring the solution at room temperature and passing through the solution constant current of 50 mA at an electric charge of 3 F/mol and a terminal voltage of 3.5 to 3.7. After passing the current, the reaction liquid was concentrated at reduced pressure. The residue was extracted with dichloromethane. The extract was concentrated at reduced pressure, thereby recovering 250 mg of a crude product.

The crude product was purified by alumina column chromatography using a 10:1 benzene-ethyl acetate mixture, giving 242 g of 2,6-diisopropoxy-4-ethoxy-4-methylhexadienone as white crystals in 93% of theoretical yield.

The compound thus obtained was identified by NMR.

NMR (CDCl$_3$): δ1.25 (t, 3H, CH$_3$), 1.30 (d, 12H, CH$_3$), 1.50 (s, 3H, CH$_3$), 3.39 (q, 2H, CH$_3$O), 4.30 (m, 2H, HCO), 5.65 (s, 2H, HC=).

EXAMPLE 5

A 252 mg quantity of 2,6-dibutoxy-4-methylphenol and 20 mg of sodium acetate were dissolved in 10 ml of methanol. Electrolysis was conducted by immersing in the solution a carbon electrode as the anode and a stainless steel electrode as the cathode each having an electrolytic area of 3 cm$^2$, stirring the solution at room temperature and passing through the solution constant current of 30 mA at an electric charge of 3 F/mol and a terminal voltage of 4.1 to 4.2 V. After passing the current, the reaction liquid was concentrated at reduced pressure. The residue was extracted with dichloromethane. The extract was concentrated at reduced pressure, thereby recovering 270 mg of a crude product.

The crude product was purified by alumina column chromatography using a 10:1 benzene-ethyl acetate mixture, giving 254 mg of 2,6-dibutoxy-4-methoxy-4-methylcyclohexadienone as white crystals in 93% of theoretical yield. The compound thus obtained was identified by NMR.

NMR (CDCl$_3$): δ1.33 (s, 18H, CH$_3$), 1.51 (s, 3H, CH$_3$), 3.17 (s, 3H, CH$_3$O), 5.65 (s, 2H, HC=).

EXAMPLE 6

A 198 mg quantity of 2,4,6-trimethoxy-4-methyl-2,5-cyclohexadienone and 10 ml of benzene were dissolved in 10 ml of concentrated sulfuric acid, and stirred at room temperature for 2 hours. Thereafter the solution was neutralized by adding sodium hydrogen carbonate to the solution and filtered. The filtrate was concentrated at reduced pressure. The residue was extracted with dichloromethane, the solvent was removed at reduced pressure and the resulting residue was concentrated, thereby recovering 158 mg of an oily crude product. The crude product was purified by silica gel column chromatography using a 20:1 benzene-ethyl acetate mixture, giving 153 mg of 2,6-dimethoxy-4-methylidene-2,5-cyclohexadienone in 92% of theoretical yield. The compound thus obtained was identified by NMR.

NMR (CDCl$_3$): δ3.79 (s, 6H, CH$_3$O), 5.50 (m, 2H, HC=), 6.25 (m, 2H, H$_2$C=).

EXAMPLE 7

The same procedure as in Example 6 was repeated by using 226 mg of 2,6-diethoxy-4-methoxy-4-methyl-2,5-cyclohexadienone and 10 mg of perchloric acid, recovering 180 mg of an oily crude product. The crude product was purified by silica gel column chromatography using a 20:1 benzene-ethyl acetate mixture, giving 175 mg of 2,6-diethoxy-4-methylidene-2,5-cyclohexadienone in 90% of theoretical yield. The compound thus obtained was identified by NMR.

NMR (CDCl$_3$): δ1.29 (t, 6H, CH$_3$), 3.92 (q, 4H, CH$_2$O), 5.54 (m, 2H, HC=), 6.20 (m, 2H, H$_2$C=).

EXAMPLE 8

The procedure of Example 6 was repeated by using 250 mg of 2,6-dibutoxy-4-methoxy-4-methyl-2,5-cyclohexadienone and 20 mg of aluminum chloride, recovering 234 g of an oily crude product. The crude product was purified by silica gel column chromatography using a 20:1 benzene-ethyl acetate mixture, giving 217 mg of 2,6-dibutoxy-4-methylidene-2,5-cyclohexadienone in 87% of theoretical yield. The compound thus obtained was identified by NMR.

NMR (CDCl$_3$): δ1.30 (s, 18H, CH$_3$), 5.48 (m, 2H, HC=), 6.25 (m, 2H, H$_2$C=).

EXAMPLE 9

A 6 mg quantity of concentrated sulfuric acid was added to a solution of 244 mg of 1,3,5,6,6-pentamethoxy-3-methyl-1,4-cyclohexadiene and 10 ml of chloroform. Then the mixture was stirred at room temperature for 1 hour. Thereafter the reaction mixture was neutralized by adding sodium hydrogen carbonate and filtered. The filtrate was concentrated at reduced pressure. The residue was extracted with dichloromethane, the solvent was removed at reduced pressure and the residue was concentrated, recovering 210 mg of an oily crude product. The crude product was purified by silica gel column chromatography using a 20:1 benzene-ethyl acetate mixture, giving 197 mg of 1,5,6,6-tetramethoxy-3-methylidene-1,4-cyclohexadiene in 93% of theoretical yield. The compound thus obtained was identified by NMR.

NMR (CDCl$_3$): δ3.20 (s, 6H, CH$_3$O), 3.77 (s, 6H, CH$_3$OC=), 4.97 (bs, 2H, HC=), 5.82 (bs, 2H, H$_2$C=).

EXAMPLE 10

The same procedure as in Example 9 was repeated using 272 mg of 1,5,6-trimethoxy-3,6-diethoxy-3-methyl-1,4-cyclohexadiene, 10 mg of methylene chloride and 10 mg of perchloric acid recovering 230 mg of an oily crude product. The crude product was purified by silica gel column chromatograph using a 20:1 benzeneethyl acetate mixture giving 220 mg of 1,5,6-trimethoxy-6-ethoxy-3-methylidene-1,4-cyclohexadiene in 92% of theoretical yield. The compound thus obtained was identified by NMR.

NMR (CDCl$_3$): δ1.25 (t, 6H, CH$_3$), 3.42 (q, 4H, CH$_2$), 3.75 (s, 6H, CH$_3$O), 4.95 (bs, 2H, HC=), 5.79 (bs, 2H, H$_2$C=).

EXAMPLE 11

The procedure of Example 9 was repeated by using 334 mg of 1,5,6-tributoxy-3,6-dimethoxy-3-methyl-1,4-cyclohexadiene, 10 ml of ether and 15 mg of aluminum chloride, recovering 290 mg of an oily crude product. The crude product was purified by silica gel column chromatography using a 20:1 benzene-ethyl acetate mixture, giving 268 mg of 1,5,6-tributoxy-6-methoxy-3-methylidene-1,4-cyclohexadiene in 89% of the theoretical yield. The compound thus obtained was identified by NMR.

NMR (CDCl$_3$): δ1.30 (s, 18H, CH$_3$C), 3.24 (s, 6H, CH$_3$O), 4.94 (bs, 2H, HC=), 5.80 (bs, 2H, H$_2$O=).

INDUSTRIAL APPLICABILITY

The cyclohexadiene derivatives of the formula (I) are useful as intermediates for synthesizing 3,4,5-trialkoxybenzaldehyde, 3,5-dialkoxy-4-hydroxybenzaldehyde, 3,4,5-trialkoxybenzylalcohol and 3,4,5-trialkoxybenzylhalide which are useful as materials for synthesis of medicinal compositions. These compounds can be derived from the compounds of this invention for example by the process shown by the reaction equation below.

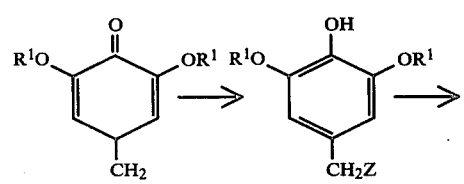

-continued

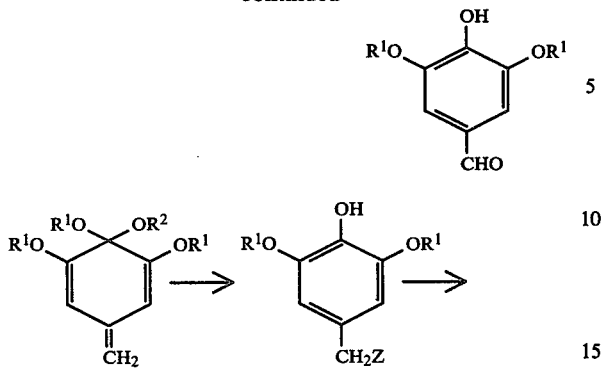

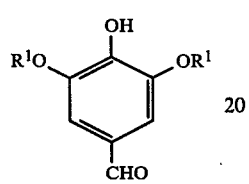

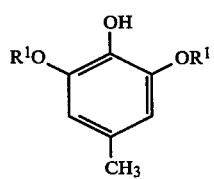

(In the formulae shown above, Z represents a hydroxyl group, halogen atom, methoxy group of acetyloxy group and $R^1$ and $R^2$ are as defined above).

We claim:

1. A process for preparing cyclohexadienone derivatives represented by the formula

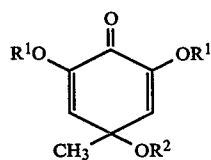

(wherein $R^1$ and $R^2$ represent a lower alkyl group), comprising the step of electrolyzing a compound of the formula

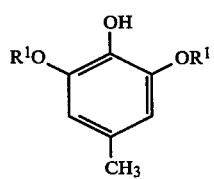

(wherein $R^1$ is as defined above) in the presence of a lower aliphatic alcohol and a neutral supporting electrolyte, to produce the cyclohexadiene derivative.

2. A process as defined in claim 1 in which the lower aliphatic alcohol is at least one member selected from the group consisting of methanol, ethanol, isopropyl alcohol and n-butyl alcohol.

3. A process as defined in claim 1 or 2 in which the neutral supporting electrolyte is at least one member selected from the group consisting of p-toluenesulfonic acid tetraalkylammonium salt, perchloric acid tetraalkylammonium salt, alkali metal salt of aliphatic carboxylic acid and alkali metal fluoride.

4. A process as defined in any of claims 1 to 3 in which the electrolytic temperature is $-10°$ to $50°$ C.

5. A process for preparing cyclohexadiene derivatives represented by the formula

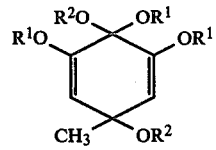

(wherein $R^1$ and $R^2$ represent a lower alkyl group), comprising the step of electrolyzing a compound of the formula

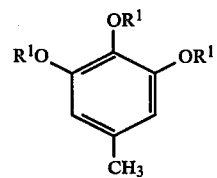

(wherein $R^1$ is as defined above) in the presence of a lower aliphatic alcohol and a neutral or alkaline supporting electrolyte to produce the cyclohexadiene derivative.

6. A process as defined in claim 5 in which the lower aliphatic alcohol is at least one member selected from the group consisting of methanol, ethanol, isopropyl alcohol and n-butyl alcohol.

7. A process as defined in claim 5 or 6 in which the neutral or alkaline supporting electrolyte is at least one member selected from the group consisting of alkali metal hydroxide, alkali metal, tetralkylammonium hydroxide, alkali metal salt of aliphatic carboxylic acid and alkali metal fluoride.

8. A process as defined in any of claims 5 to 8 in which the electrolytic temperature is $-10°$ to $50°$ C.

9. A process for preparing cyclohexadien derivatives represented by the formula

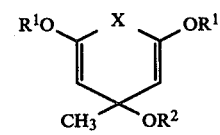

wherein X represents

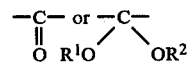

and $R^1$ and $R^2$ represent a lower alkyl group, comprising the step of electrolyzing a compound of the formula

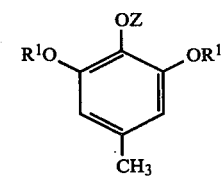

wherein Z represent H or $R^1$ and $R^1$ is as defined above, in the presence of a lower aliphatic alcohol and a neutral or alkalene electrolyte to produce the cyclohexadiene derivative.

* * * * *